(12) United States Patent
Bush et al.

(10) Patent No.: US 8,202,837 B2
(45) Date of Patent: Jun. 19, 2012

(54) METHODS FOR ADMINISTERING HYPOGLYCEMIC AGENTS

(75) Inventors: Mark A. Bush, Durham, NC (US); Mary Colleen O'Neill, San Francisco, CA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 715 days.

(21) Appl. No.: 12/092,433

(22) PCT Filed: Nov. 3, 2006

(86) PCT No.: PCT/US2006/060508
§ 371 (c)(1), (2), (4) Date: May 2, 2008

(87) PCT Pub. No.: WO2007/056681
PCT Pub. Date: May 18, 2007

(65) Prior Publication Data
US 2008/0254087 A1    Oct. 16, 2008

Related U.S. Application Data

(60) Provisional application No. 60/733,920, filed on Nov. 4, 2005, provisional application No. 60/742,600, filed on Dec. 6, 2005.

(51) Int. Cl.
*A61K 38/26* (2006.01)

(52) U.S. Cl. .................. 514/7.2; 530/324; 530/308

(58) Field of Classification Search .................. 530/324, 530/308; 514/7.2
See application file for complete search history.

(56) References Cited

U.S. PATENT DOCUMENTS

| | | | |
|---|---|---|---|
| 4,790,824 A * | 12/1988 | Morrow et al. | 604/143 |
| 5,545,618 A | 8/1996 | Buckley et al. | |
| 6,200,296 B1 * | 3/2001 | Dibiasi et al. | 604/272 |
| 6,569,143 B2 * | 5/2003 | Alchas et al. | 604/506 |
| 6,629,963 B2 * | 10/2003 | Prais et al. | 604/274 |
| 6,776,776 B2 * | 8/2004 | Alchas et al. | 604/198 |
| 6,843,781 B2 * | 1/2005 | Alchas et al. | 604/117 |
| 7,076,987 B2 * | 7/2006 | Martin et al. | 72/342.94 |
| 7,141,547 B2 | 11/2006 | Rosen et al. | |
| 7,164,005 B2 | 1/2007 | Costantino et al. | |
| 7,189,690 B2 | 3/2007 | Rosen et al. | |
| 7,235,063 B2 * | 6/2007 | D'Antonio et al. | 604/187 |
| 7,238,660 B2 | 7/2007 | Rosen et al. | |
| 7,238,667 B2 | 7/2007 | Rosen et al. | |
| 7,259,233 B2 * | 8/2007 | Dodd et al. | 530/308 |
| 7,521,424 B2 | 4/2009 | Rosen et al. | |
| 7,569,384 B2 | 8/2009 | Rosen et al. | |
| 2005/0054570 A1 | 3/2005 | Rosen et al. | |
| 2010/0009910 A1 | 1/2010 | Bush et al. | |

FOREIGN PATENT DOCUMENTS

EP    1408050 A1    4/2004

OTHER PUBLICATIONS

Knudsen (J Med Chem 43, 1664, 2000).*
Greig (Diabetologia 42, 45-50, 1999).*
Hamilton, James G., The Journal of Family Practice 41(2), 169-175 (1995).*
Tattersall R.B., (Diabetologia 20, 517-523, 1981).*
Stark M. M. (Journal of clinical forensic medicine 7(1), 35-38, 2000).*
Maniatis A. K. (Pediatric diabetes 2(2), 51-57, 2001).*
Mumford Owen (The Diabetes Educator 30(2), 174, 2004).*
Smalley A (Paediatric Nursing 11(2), 17-20, 1999).*
Zambanini A (Diabetic medicine : a journal of the British Diabetic Association 14(4), 321-323, 1997).*
Caffrey, et al., "How to take your best shot", Diabetes Health—Investigate, Infoim, Inspire Nov. 1, 2004, XP002587054 Retrieved from the Internet: URS:http://www.diabeteshealth.com/read/2004/11/01/4128/how-to-take-your-best-shot/ [retrieved on Jun. 14, 2010].
Database Geneseq [Online] Mar. 11, 2004 "Human albumin/GLP-1(7-36(A8G)) fusion protein SEQ ID No:611." XP002587051 retrieved from EBI accession No. GSP:ADH2181.
Database Geneseq [Online] Apr. 15, 1997 "Glucagon like peptide 1 (7-37) analogue Gly8." XP002587052 from EBI accession No. GSP:AAW03783.
Database Geneseq [Online] Oct. 21, 2004, "Human insulinotropic GLP-1(7-36) analogue polypeptide, Gly8-GLP-1(7-36)." XIP002587053 retrieved from EBI accession No. GSP:ADR00560.

* cited by examiner

*Primary Examiner* — David Lukton
(74) *Attorney, Agent, or Firm* — Edward R. Gimmi; Andrea V. Lockenour

(57) ABSTRACT

The present invention relates to methods of administering hypoglycemic agents and/or GLP-1 agonists.

29 Claims, 2 Drawing Sheets

Figure 2

SEQ ID NO.: 1

```
HGEGTFTSDVSSYLEGQAAKEFIAWLVKGRHGEGTFTSDVSSYLEGQAAKEFIAWLVKGR  60
DAHKSEVAHRFKDLGEENFKALVLIAFAQYLQQCPFEDHVKLVNEVTEFAKTCVADESAE 120
NCDKSLHTL FGDKLCTVATLRETYGEMADCCAKQEPERNECFLQHKDDNPNLPRLVRPE 180
VDVMCTAFHDNEETFLKKYLYEIARRHPYFYAPELLFFAKRYKAAFTECCQAADKAACLL 240
PKLDELRDEGKASSAKQRLKCASLQKFGERAFKAWAVARLSQRFPKAEFAEVSKLVTDLT 300
KVHTECCHGDLLECADDRADLAKYICENQDSISSKLKECCEKPLLEKSHCIAEVENDEMP 360
ADLPSLAADFVESKDVCKNYAEAKDVFLGMFLYEYARRHPDYSVVLLLRLAKTYETTLEK 420
CCAAADPHECYAKVFDEFKPLVEEPQNLIKQNCELFEQLGEYKFQNALLVRYTKKVPQVS 480
TPTLVEVSRNLGKVGSKCCKHPEAKRMPCAEDYLSVVLNQLCVLHEKTPVSDRVTKCCTE 540
SLVNRRPCFSALEVDETYVPKEFNAETFTFHADICTLSEKERQIKKQTALVELVKHKPKA 600
TKEQLKAVMDDFAAFVEKCCKADDKETCFAEEGKKLVAASQAALGL              674
```

US 8,202,837 B2

SEQUENCE LISTING

<160> NUMBER OF SEQ ID NOS: 1

<210> SEQ ID NO 1
<211> LENGTH: 645
<212> TYPE: PRT
<213> ORGANISM: Homo sapiens

<400> SEQUENCE: 1

```
His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg Asp Ala His Lys
    50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Cys Pro Phe
                85                  90                  95

Glu Asp His Val Lys Leu Val Asn Glu Val Thr Glu Phe Ala Lys Thr
            100                 105                 110

Cys Val Ala Asp Glu Ser Ala Glu Asn Cys Asp Lys Ser Leu His Thr
        115                 120                 125

Leu Phe Gly Asp Lys Leu Cys Thr Val Ala Thr Leu Arg Glu Thr Tyr
    130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
            180                 185                 190

Thr Phe Leu Lys Lys Tyr Leu Tyr Glu Ile Ala Arg Arg His Pro Tyr
        195                 200                 205

Phe Tyr Ala Pro Glu Leu Leu Phe Phe Ala Lys Arg Tyr Lys Ala Ala
    210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255

Arg Leu Lys Cys Ala Ser Leu Gln Lys Phe Gly Glu Arg Ala Phe Lys
            260                 265                 270
```

-continued

```
Ala Trp Ala Val Ala Arg Leu Ser Gln Arg Phe Pro Lys Ala Glu Phe
        275                 280                 285
Ala Glu Val Ser Lys Leu Val Thr Asp Leu Thr Lys Val His Thr Glu
    290                 295                 300
Cys Cys His Gly Asp Leu Leu Glu Cys Ala Asp Asp Arg Ala Asp Leu
305                 310                 315                 320
Ala Lys Tyr Ile Cys Glu Asn Gln Asp Ser Ile Ser Ser Lys Leu Lys
                325                 330                 335
Glu Cys Cys Glu Lys Pro Leu Leu Glu Lys Ser His Cys Ile Ala Glu
            340                 345                 350
Val Glu Asn Asp Glu Met Pro Ala Asp Leu Pro Ser Leu Ala Ala Asp
        355                 360                 365
Phe Val Glu Ser Lys Asp Val Cys Lys Asn Tyr Ala Glu Ala Lys Asp
    370                 375                 380
Val Phe Leu Gly Met Phe Leu Tyr Glu Tyr Ala Arg Arg His Pro Asp
385                 390                 395                 400
Tyr Ser Val Val Leu Leu Leu Arg Leu Ala Lys Thr Tyr Glu Thr Thr
                405                 410                 415
Leu Glu Lys Cys Cys Ala Ala Ala Asp Pro His Glu Cys Tyr Ala Lys
            420                 425                 430
Val Phe Asp Glu Phe Lys Pro Leu Val Glu Glu Pro Gln Asn Leu Ile
        435                 440                 445
Lys Gln Asn Cys Glu Leu Phe Glu Gln Leu Gly Glu Tyr Lys Phe Gln
    450                 455                 460
Asn Ala Leu Leu Val Arg Tyr Thr Lys Lys Val Pro Gln Val Ser Thr
465                 470                 475                 480
Pro Thr Leu Val Glu Val Ser Arg Asn Leu Gly Lys Val Gly Ser Lys
                485                 490                 495
Cys Cys Lys His Pro Glu Ala Lys Arg Met Pro Cys Ala Glu Asp Tyr
            500                 505                 510
Leu Ser Val Val Leu Asn Gln Leu Cys Val Leu His Glu Lys Thr Pro
        515                 520                 525
Val Ser Asp Arg Val Thr Lys Cys Cys Thr Glu Ser Leu Val Asn Arg
    530                 535                 540
Arg Pro Cys Phe Ser Ala Leu Glu Val Asp Glu Thr Tyr Val Pro Lys
545                 550                 555                 560
Glu Phe Asn Ala Glu Thr Phe Thr Phe His Ala Asp Ile Cys Thr Leu
                565                 570                 575
Ser Glu Lys Glu Arg Gln Ile Lys Lys Gln Thr Ala Leu Val Glu Leu
            580                 585                 590
Val Lys His Lys Pro Lys Ala Thr Lys Glu Gln Leu Lys Ala Val Met
        595                 600                 605
Asp Asp Phe Ala Ala Phe Val Glu Lys Cys Cys Lys Ala Asp Asp Lys
    610                 615                 620
Glu Thr Cys Phe Ala Glu Glu Gly Lys Lys Leu Val Ala Ala Ser Gln
625                 630                 635                 640
Ala Ala Leu Gly Leu
                645
```

METHODS FOR ADMINISTERING HYPOGLYCEMIC AGENTS

This Application is a §371 of International Application No. PCT/US2006/060508, filed 3 Nov. 2006, which claims priority of U.S. Provisional Application No. 60/733,920, filed 4 Nov. 2005 and U.S. Provisional Application No. 60/742,600, filed 6 Dec. 2005.

BACKGROUND

Hypoglycemic agents may be used in the treatment of both Type I and Type II diabetes to lower glucose concentration in blood. Insulinotropic peptides have been implicated as possible therapeutic agents for the treatment of diabetes. Insulinotropic peptides include incretin hormones such as, but are not limited to, gastric inhibitory peptide (GIP) and glucagon like peptide-1 (GLP-1) as well as fragments, variants, and conjugates thereof. Insulinotropic peptides also include exendin 3 and exendin 4. GLP-1 is a 30 amino acid long incretin hormone secrected by the L-cells in the intestine. GLP-1 has been shown to stimulate insulin secretion in a physiological and glucose-dependent manner, decrease glucagon secretion, inhibit gastric emptying, decrease appetite, and stimulate proliferation of β-cells.

Insulin and insulinotrpoic peptides may be administered via subcutaneous injection, such as with a needle containing device, for example, a pen injector, and/or syringe. Patients may need to inject several times a day to control blood glucose, which can be burdensome as well as painful. Thus, there is a need for methods of administering hypoglycemic agents less frequently and by methods that will minimize such burdensome regimens as well as site injection pain.

SUMMARY OF THE INVENTION

In one embodiment of the present invention, methods are provided for administering a GLP-1 agonist composition comprising at least one polypeptide to a patient in need thereof, comprising the step of injecting the GLP-1 agonist composition via an injection device comprising a tube having a gauge of about 28 or greater, wherein said polypeptide is administered no more than once daily. The polypeptide may be, but is not limited to, GLP-1 or a fragment, variant, and/or conjugate thereof. Certain embodiments of a GLP-1 or a fragment, variant, or conjugate thereof comprise human serum albumin. Human serum albumin, variants and/or fragments thereof, may be conjugated to a GLP-1 or fragment or variant thereof. Human serum albumin may be conjugated through a chemical linker, including but not limited to naturally occurring or engineered disulfide bonds, or by genetic fusion to GLP-1, or a fragment or variant thereof.

In another aspect of the present invention, methods are provided for administering a hypoglycemic agent comprising at least one polypeptide to a patient in need thereof, comprising the step of injecting the hypoglycemic agent via an injection device comprising a tube having a gauge of about 28 or greater, wherein said polypeptide is administered no more than once daily.

In another aspect of the present invention, methods are provided for treating or preventing a disease in a mammal in need thereof comprising administering a composition comprising at least one polypeptide having GLP-1 agonist activity once weekly, wherein the composition comprises about 0.25 mg to about 104 mg of at least one polypeptide having GLP-1 activity. The mammal may suffer from one or more of the following diseases: Type 1 diabetes, Type II diabetes, obesity and hyperglycemia.

BRIEF DESCRIPTION OF THE DRAWINGS

FIG. 2: SEQ ID NO:1 which comprises two tandemly oriented GLP-1(7-36)(A8G) fused to the N-Terminus of human serum albumin.

DEFINITIONS

Figure 1:
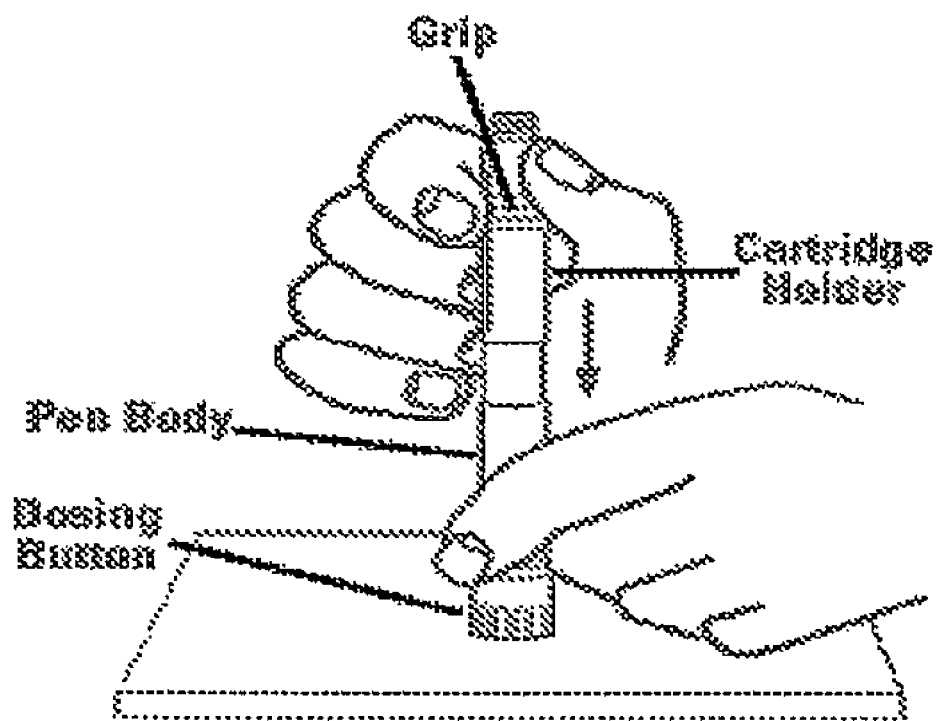
FIG. 1: A device for delivery of lyophilized hypoglycemic agent and/or GLP-1 agonist

"GLP-1 agonist composition" as used herein means any composition capable of stimulating the secretion of insulin, including, but not limited to an incretin hormone.

"Incretin hormone" as used herein means any hormone that potentiates insulin secretion. One example of an incretin hormone is GLP-1. GLP-1 is an incretin secreted by intestinal L cells in response to ingestion of food. In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying time and slows small bowel motility delaying food absorption. GLP-1 promotes continued beta cell competence by stimulating transcription of genes involved in glucose dependent insulin secretion and by promoting beta-cell neogenesis (Meier, et al. "Glucagon-Like Peptide 1 and Gastric Inhibitory Polypeptide Potential Applications in Type 2 Diabetes Mellitus" *Biodrugs* 2003; 17 (2): 93-102).

"GLP-1 activity" as used herein means one or more of the activities of naturally occurring human GLP-1, including but not limited to, stimulating glucose-dependent insulin secretion, suppressing glucagon secretion, delaying gastric emptying, and promoting beta cell competence and neogenesis.

An "incretin mimetic" as used herein is a compound capable of potentiating insulin secretion. An incretin mimetic may be capable of stimulating insulin secretion, increasing beta cell neogenesis, inhibiting beta cell apoptosis, inhibiting glucagon secretion, delaying gastric emptying and inducing satiety in a mammal. An incretin mimetic may include, but is not limited to, any polypeptide which has GLP-1 activity, including but not limited to, exendin 3 and exendin 4, including any fragments and/or variants and/or conjugates thereof.

"Hypoglycemic agent" as used herein means any compound or composition comprising a compound capable of reducing blood glucose. A hypoglycemic agent may include, but is not limited to, any GLP-1 agonist including incretin hormones or incretin mimetics, GLP-1 or fragment, variant and/or conjugate thereof. Other hypoglycemic agents include, but are not limited to, drugs that increase insulin secretion (e.g., sulfonylureas (SU) and meglitinides), increase glucose utilization (e.g., glitazones), reduce hepatic glucose production (e.g., metformin), and delay glucose absorption (e.g., c-glucosidase inhibitors).

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques that are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W.H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth. Enzymol.* (1990) 182:626-646 and Rattan, et al., "Protein Synthesis: Posttranslational Modifications and Aging", *Ann NY Acad Sci* (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

As used herein "conjugate" or "conjugated" refers to two molecules that are bound to each other. For example, a first polypeptide may be covalently or non-covalently bounded to a second polypeptide. The first polypeptide may be covalently bound by a chemical linker or may be fused genetically to the second polypeptide, wherein the first and second polypeptide share a common polypeptide backbone.

As used herein "tandemly oriented" refers to two or more polypeptides that are adjacent to one another as part of the same molecule. They may be linked either covalently or non-covalently. Two or more tandemly oriented polypeptides may form part of the same polypeptide backbone. Tandemly oriented polypeptides may have direct or inverted orientation and/or may be separated by other amino acid sequences.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-30 of naturally occurring GLP-1 may also be a variant having amino acid substitutions within its partial sequence.

As used herein, "reduce" or "reducing" blood glucose refers to a decrease in the amount of blood glucose observed in the blood of a patient after administration a hypoglycemic agent.

As used herein "disease associated with elevated blood glucose" include, but are not limited to, Type I and Type II diabetes and hyperglycemia.

As used herein "co-administration" or "co-administering" as used herein refers to administration of two or more compounds to the same patient. Co-administration of such compounds may be at about the same time (e.g., within the same hour) or it may be within several hours or days of one another. For example, a first compound may be administered once weekly while a second compound is co-administered daily.

DETAILED DESCRIPTION OF THE INVENTION

In one embodiment of the present invention, methods are provided for administering a GLP-1 agonist composition comprising at least one polypeptide to a patient in need thereof, comprising the step of injecting the GLP-1 agonist composition via an injection device comprising a tube having a gauge of about 28 or greater, wherein said polypeptide is administered no more than once daily. As is understood in the art, examples of needles with gauges of 28 or greater include, but are not limited to, 28, 29 and 30 gauge needles. As is also understood in the art, the higher the needle gauge the smaller the needle aperture. An embodiment of the invention comprises a polypeptide that may be, but is not limited to, GLP-1 or a fragment, variant, or conjugate thereof. A GLP-1 or a fragment, variant, or conjugate thereof may comprise human serum albumin. Human serum albumin may be conjugated to the GLP-1 or fragment or variant thereof. Human serum albumin may be conjugated through a chemical linker or genetically fused to the GLP-1 fragment or variant. Examples of GLP-1, fragments or variants, fused with human serum albumin are provided in the following PCT applications: WO 2003/060071, WO 2003/59934, WO 2005/003296, WO 2005/077042.

A further embodiment of the invention comprises one, two, three, four, five, or more tandemly oriented molecules of GLP-1 fused to the N- or C-terminus of human serum albumin or variant thereof. GLP-1 fragments may include, but are not limited to, molecules of GLP-1 comprising, or alternatively consisting of, amino acids 7 to 36 of GLP-1 (hereinafter designated as "GLP-1 (7-36)"). Variants of GLP-1 or fragments of GLP-1 may include, but are not limited to, substitutions of an alanine residue analogous to alanine 8 of wild type GLP-1, such alanine being mutated to a glycine (hereinafter designated as "A8G") (See for Example, the mutants disclosed in U.S. Pat. No. 5,545,618, herein incorporated by reference in its entirety). Other embodiments have such A8G polypeptides fused to the N- or C-terminus of albumin or variant thereof. An example of two tandemly oriented GLP-1(7-36)(A8G) fragments/variants fused to the N-terminus of human serum albumin comprises SEQ ID NO: 1, which is presented in FIG. 2.

In another aspect of the present invention, the GLP-1 agonist composition further comprises one or more compounds selected from the group of: peroxisome proliferating activated receptor (PPAR) ligand, thiazolidinedione, metformin, insulin, and sulfonylurea. In another aspect, methods are provided comprising the step of co-administering at least one GLP-1 agonist with one or more compounds selected from the group of: peroxisome proliferating activated receptor (PPAR) ligand, thiazolidinedione, metformin, insulin, and sulfonylurea. The GLP-1 agonist composition may have one or more of these compounds in addition to at least one polypeptide.

In another aspect, the GLP-1 agonist composition is lyophilized. In another aspect of this invention, methods are provided that further comprise admixing said GLP-1 agonist composition with a liquid prior to administration of said GLP-1 agonist composition. In yet another aspect, the GLP-1 agonist composition is in solution form, and may be an aqueous solution.

In yet another aspect of the present invention, at least one polypeptide of a GLP-1 agonist composition may be administered to said patient once weekly, twice weekly, once every two weeks, and/or once monthly. In another aspect, the patient suffers from Type II diabetes. An injection device of the invention may be reusable and/or disposable. In one aspect, an injection device comprises a needle. In another aspect the injection a delivery device of the invention comprises a catheter.

In yet another aspect, GLP-1 agonist composition is administered via subcutaneous injection. In another aspect, the injection may be intramuscular or intravenous, intraperitoneal, intranasal, transmucosal or topical. In another aspect, GLP-1 agonist composition is self-administered, meaning a patient receiving an injection administers a GLP-1 agonist composition to himself or herself. Subcutaneous, injections may be administered, for example, at the abdomen, upper arm, and/or thigh.

In another aspect of the present invention, methods are provided for administering a hypoglycemic agent comprising at least one polypeptide to a patient in need thereof, comprising the step of injecting a hypoglycemic agent via an injection device comprising a tube having a gauge of about 28 or greater, wherein said polypeptide is administered no more than once daily. The needle may have a 29 or 30 gauge. In another aspect, the polypeptide of the invention is not insulin.

In another aspect of the present invention methods are provided for treating or preventing a disease in a mammal in need thereof comprising administering a composition comprising at least one polypeptide having GLP-1 agonist activity once weekly, wherein the composition comprises about 0.010 mg to about 104 mg of at least one polypeptide having GLP-1 activity. The disease may be selected from the group consisting of Type 1 diabetes, Type II diabetes, obesity and hyperglycemia. In one aspect, the disease is Type II diabetes.

In another aspect of the present invention, the polypeptide having GLP-1 activity comprises at least one fragment or variant of human GLP-1 genetically fused with human serum albumin. This fragment or variant of GLP-1 may comprise GLP-1(7-36(A8G)). At least one fragment or variant of GLP-1 may be genetically fused to human serum albumin. In another aspect, the polypeptide having GLP-1 activity comprises at least two GLP-1(7-36(A8G)) tandemly and genetically fused to the human serum albumin. In another aspect, the two GLP-1(7-36(A8 G)) are genetically fused at the N-terminus of the human serum albumin. In another aspect, at least one polypeptide having GLP-1 activity comprises SEQ ID No.: 1. At least one polypeptide having GLP-1 activity may be administered at a dose of about 0.25 mg to about 32 mg weekly. Some examples of doses for a once weekly administration of a polypeptide having GLP-1 activity include, but are not limited to, 0.010 mg/week, 0.25 mg/week, 0.5 mg/week, 0.8 mg/week, 1.0 mg/week, 2 mg/week, 3.2 mg/week, 8 mg/week, 12.8 mg/week, 32 mg/week, 51.2 mg/week, and/or 104 mg/week.

EXAMPLES

The following examples illustrate various aspects of this invention. These examples do not limit the scope of this invention which is defined by the appended claims.

Example 1

The following devices may be used to deliver a hypoglycemic and/or a GLP-1 agonist composition:
1. STATdose®, GSK, Liquid Drug Product Reusable Auto-injector;
2. Autoject Mini®, Owen Mumford, Liquid Drug Product Reusable Auto-injector,
3. Penlet®, Becton Dickinson, Liquid Drug Product Disposable Auto-injector;
4. Tigerlily/Snapdragon®, Owen Mumford, Liquid Drug Product Disposable Auto-injector;
5. AutoSafety Injector®, The Medical House, Liquid Drug Product Disposable Auto-injector;
6. Liquid Dry Injector® Becton Dickinson, Lyophilised Drug Product Disposable Pen Injector; and/or
7. Pre-filled syringes.

Example 2

A lyophilized hypoglycemic agent and/or GLP-1 agonist composition may be delivered by a device as shown in FIG. 1. This device system can contain a powder comprising a lyophilized hypoglycemic agent and/or GLP-1 agonist and a liquid. This device system can be held upright to mix a contained powder and liquid. The two halves of an injection pen can be pressed together firmly until the powder completely dissolves. Once dissolved the hypoglycemic agent and/or GLP-1 agonist composition can be administered to the patient.

Example 3

A hypoglycemic agent and/or GLP-1 agonist composition can comprise a polypeptide having GLP-1 activity. A hypoglycemic agent and/or GLP-1 agonist composition comprising a polypeptide having GLP-1 activity can be delivered by subcutaneous injection to a person in need thereof, wherein the agent or composition comprises polypeptide having GLP-1 activity at a dose in the range of about 0.010 mg to about 104 mg once weekly. Some examples of doses for a once weekly administration of a GLP-1 agonist composition comprising a polypeptide having GLP-1 activity include, but are not limited to, 010 mg/week, 0.25 mg/week, 0.5 mg/week, 0.8 mg/week, 1.0 mg/week, 2 mg/week, 3.2 mg/week, 8 mg/week, 12.8 mg/week, 32 mg/week, 51.2 mg/week, and/or 104 mg/week.

Example 4

A lyophilized hypoglycemic agent and/or GLP-1 agonist composition can be reconstituted with water for injection. Examples of excipients that can be included in the composition include, but are not limited to, trehalose dehydrate, mannitol, sodium phosphate (such as dibasic, anhydrous and monobasic, monohydrate), polysorbate 80, sodium hydroxide, phosphoric acid, and water for injection.

All patent applications to which this application claims priority are incorporated by reference herein in their entirety as if each application is specifically and individually being fully set forth.

We claim:

1. A method of administering a GLP-1 agonist composition comprising at least one polypeptide to a patient in need thereof, comprising the step of injecting the GLP-1 agonist composition as a subcutaneous injection to said patient via an injection device comprising a tube having a gauge of about 28 or greater, wherein said polypeptide is administered as a subcutaneous injection once weekly and wherein said composition comprises about 0.01 mg to about 104 mg of said polypeptide.

2. The method of claim 1, wherein said at least one polypeptide comprises GLP-1 or a fragment, variant, or conjugate thereof.

3. The method of claim 2, wherein the GLP-1 or a fragment, variant, or conjugate thereof further comprises human serum albumin.

4. The method of claim 3, wherein the human serum albumin is conjugated to the GLP-1 or fragment or variant thereof.

5. The method of claim 1, wherein the GLP-1 agonist composition further comprises a compound selected from the group of: peroxisome proliferating activated receptor ligand, thiazolidinedione, metformin, insulin, and sulfonylurea.

6. The method of claim 1, wherein the GLP-1 agonist composition is lyophilized.

7. The method of claim 6, further comprising admixing said GLP-1 agonist composition with a liquid prior to administration of said GLP-1 agonist composition.

8. The method of claim 1, wherein the GLP-1 agonist composition is in liquid form.

9. A method of administering a GLP-1 agonist composition comprising at least one polypeptide to a patient in need thereof, comprising the step of injecting the GLP-1 agonist composition as a subcutaneous injection to said patient via an injection device comprising a tube having a gauge of about 28 or greater, wherein said polypeptide is administered as a subcutaneous injection once monthly and wherein said composition comprises about 0.01 mg to about 104 mg of said polypeptide.

10. The method of claim 1, wherein the patient has Type II diabetes.

11. The method of claim 1, wherein the injection device is reusable.

12. The method of claim 1, wherein the injection device is disposable.

13. The method of claim 1, wherein the injection device comprises a needle.

14. The method of claim 1, wherein the injection device comprises a catheter.

15. The method of claim 1 wherein said GLP-1 agonist composition is self-administered.

16. The method of claim 1, further comprising the step of co-administering a compound selected from the group of: peroxisome proliferating activated receptor ligand, thiazolidinedione, metformin, insulin, and sulfonylurea.

17. A method for treating a disease selected from the group consisting of Type 1 diabetes, Type II diabetes, obesity and hyperglycemia in a mammal in need thereof comprising administering a composition comprising at least one polypeptide having GLP-1 activity as a subcutaneous injection to said mammal via an injection device comprising a tube having a gauge of about 28 or greater once weekly, wherein the composition comprises about 0.01 mg to about 104 mg of at least one polypeptide having GLP-1 activity.

18. The method of claim 17 wherein the disease is Type II diabetes.

19. The method of claim 17, wherein the polypeptide having GLP-1 activity comprises at least one fragment or variant of human GLP-1 genetically fused with human serum albumin.

20. The method of claim 19 wherein the at least one fragment or variant of GLP-1 comprises GLP-1(7-36(A8G)).

21. The method of claim 20 wherein the at least one fragment or variant of GLP-1 is genetically fused to human serum albumin.

22. The method of claim 21 wherein at least one fragment or variant of GLP-1 comprises at least two GLP-1(7-36(A8G)) tandemly and genetically fused to the human serum albumin.

23. The method of claim 21 wherein the at least two GLP-1(7-36(A8G)) are genetically fused at the N-terminus of the human serum albumin.

24. The method of claim 17 wherein at least one polypeptide having GLP-1 activity comprises the amino acid sequence of SEQ ID NO: 1.

25. The method of claim 24 wherein at least one polypeptide having GLP-1 activity is administered at a dose of about 0.25 mg to about 32 mg weekly.

26. The method of claim 1, wherein said GLP-1 agonist composition comprises said polypeptide in an amount of about 2 mg.

27. The method of claim 26, wherein said GLP-1 agonist composition comprises exendin-4.

28. The method of claim 1, wherein said GLP-1 agonist composition comprises the amino acid sequence of SEQ ID NO:1.

29. The method of claim 28, wherein said amino acid sequence of SEQ ID NO:1 is present in said injection in an amount of about 0.25 mg to about 32 mg.

* * * * *